US011452632B2

(12) United States Patent
Kramer et al.

(10) Patent No.: US 11,452,632 B2
(45) Date of Patent: Sep. 27, 2022

(54) ABDOMINAL SACRAL WAIST SUPPORT BELT

(71) Applicant: Orthotic Solutions, LLC, Blaine, MN (US)

(72) Inventors: Thomas Kramer, Andover, MN (US); Patrick Scott Hinshon, Morris, MN (US)

(73) Assignee: Orthotic Solutions, LLC, Minneapolis, MN (US)

( * ) Notice: Subject to any disclaimer, the term of this patent is extended or adjusted under 35 U.S.C. 154(b) by 9 days.

(21) Appl. No.: 16/612,741

(22) PCT Filed: May 11, 2018

(86) PCT No.: PCT/US2018/032470
§ 371 (c)(1),
(2) Date: Nov. 11, 2019

(87) PCT Pub. No.: WO2018/209326
PCT Pub. Date: Nov. 15, 2018

(65) Prior Publication Data
US 2020/0060860 A1    Feb. 27, 2020

Related U.S. Application Data

(60) Provisional application No. 62/505,379, filed on May 12, 2017.

(51) Int. Cl.
*A61F 5/03*    (2006.01)
*A61F 5/28*    (2006.01)
(Continued)

(52) U.S. Cl.
CPC ............... *A61F 5/028* (2013.01); *A61F 5/32* (2013.01)

(58) Field of Classification Search
CPC .. A61F 5/32; A61F 5/022; A61F 5/024; A61F 5/026; A61F 5/028; A61F 5/03;
(Continued)

(56) References Cited

U.S. PATENT DOCUMENTS 5,135,471 A * 8/1992 Houswerth ............ A61F 5/024
602/19
5,599,287 A * 2/1997 Beczak, Sr. ........... A61F 5/026
128/105.1
(Continued)

*Primary Examiner* — Camtu T Nguyen
(74) *Attorney, Agent, or Firm* — Craig J. Lervick; Larkin Hoffman Daly & Lindgren, Ltd.

(57) ABSTRACT

In order to provide efficient support for a user's back, the belt of the present application includes structures to help align and maintain the position of three portions of the users body—an upper abdominal region, a lower abdominal region and the lower back. To provide this support, a belt has an abdominal panel configured to be positioned over the user's abdomen, and a belt member wrapping around the waist region. The abdominal panel has a specific configuration and size to cause an upper portion of the abdomen is held in position and a lower portion of the abdomen to be held in position, with forces being applied so that these portions remain in a preferred alignment. The belt member includes a strap that is configured so that it can be positioned within the user's waist groove, and will provide additional supporting forces. In this way, the belt provides support to three critical locations on the user's body, thus insuring optimum alignment and support of the user's central body region.

12 Claims, 4 Drawing Sheets

(51) Int. Cl.
*A61F 5/02* (2006.01)
*A61F 5/32* (2006.01)

(58) Field of Classification Search
CPC ........... A43C 11/165; A44C 5/18; A44C 5/22; A42B 3/08; A42B 3/145; Y10T 24/4782; Y10T 24/47; G04B 37/18
See application file for complete search history.

(56) References Cited

U.S. PATENT DOCUMENTS

| | | | | |
|---|---|---|---|---|
| 5,830,168 A | * | 11/1998 | Finnell | A61F 5/0193 602/23 |
| 6,190,343 B1 | * | 2/2001 | Heinz | A61F 5/024 602/19 |
| 6,790,191 B1 | * | 9/2004 | Hendricks | A61F 5/024 602/19 |
| 8,328,742 B2 | * | 12/2012 | Bledsoe | A61F 5/028 128/846 |

* cited by examiner

ABDOMINAL SACRAL WAIST SUPPORT BELT

RELATED APPLICATIONS

This application is related to and claims the benefit of previously filed U.S. Provisional Application 62/505,379, filed May 12, 2017 and entitled "Abdominal Sacral Waist Support Belt", the entirety of which is incorporated herein by reference.

BACKGROUND

Support belts are utilized for many different purposes depending on the user's condition and the desired needs. For example, a support belt is often used to limit gross motion post operatively, provide pain control, promote healing, prevent injury, rehabilitation, and therapy. One example includes the Adjustable Lumbo Sacral Orthosis, described in detail in U.S. Pat. No. 8,920,853, which is incorporated herein by reference.

As can be appreciated, support belts may have many different applications or features, and may be applied for multiple purposes. Many existing belts provide support to the user's lumbar or lower back region, since that is a region of the body which is often strained or injured. In addition, lateral support, and abdominal support are needed in certain situations. Most existing products simply provide a circumferential squeeze to provide some level of support, which is not always optimal. Based on these various unique demands and needs, it is difficult to design a belt that is appropriate for all situations.

SUMMARY

In order to provide the appropriate levels of support and alignment of a user's lumbar and lower back region, the embodiments disclosed below provide a combination of support and pressure to specifically targeted areas of the body. As will be further described, this involves a "three-point" pressure methodology causing force to be applied to two portions of the abdominal region, and an opposing force to the users waist grove. In order to accomplish this methodology, an abdominal panel is specifically designed and configured to provide forces to an upper central and a lower central area of the abdominal region. These forces are supplied by upper and lower edges of the abdominal panel itself, and are the result of the specific configuration of the abdominal panel itself. Further, a waist grove belt is included which wraps around the users abdominal region at a specific location above the crest of the hip and below the twelfth rib. The appropriate alignment and positioning of these force causes better body alignment and posture for users and provides many benefits in the areas of pain reduction and rehabilitation.

BRIEF DESCRIPTION OF THE DRAWINGS

Further objects and advantages of the disclosed embodiment will be seen from the detailed description set forth below and the drawings in which.

DESCRIPTION OF THE EMBODIMENTS

In order to provide appropriate circumferential intracavity compression and abdominal support, the various embodiments of a support belt 10 discussed and disclosed herein provide a three point support system including a waist groove belt 20 and an abdominal panel 30 specifically designed to fit along the users waist. More specifically, waist groove belt 20 is designed to be positioned in the space below the 12th rib margin and above the hip (and even more specifically, above the crest of the pelvis). In this manner, support belt 10 will provide appropriate support and pressure is easily applied to specifically designated or targeted areas of the user's body.

Figure 1:
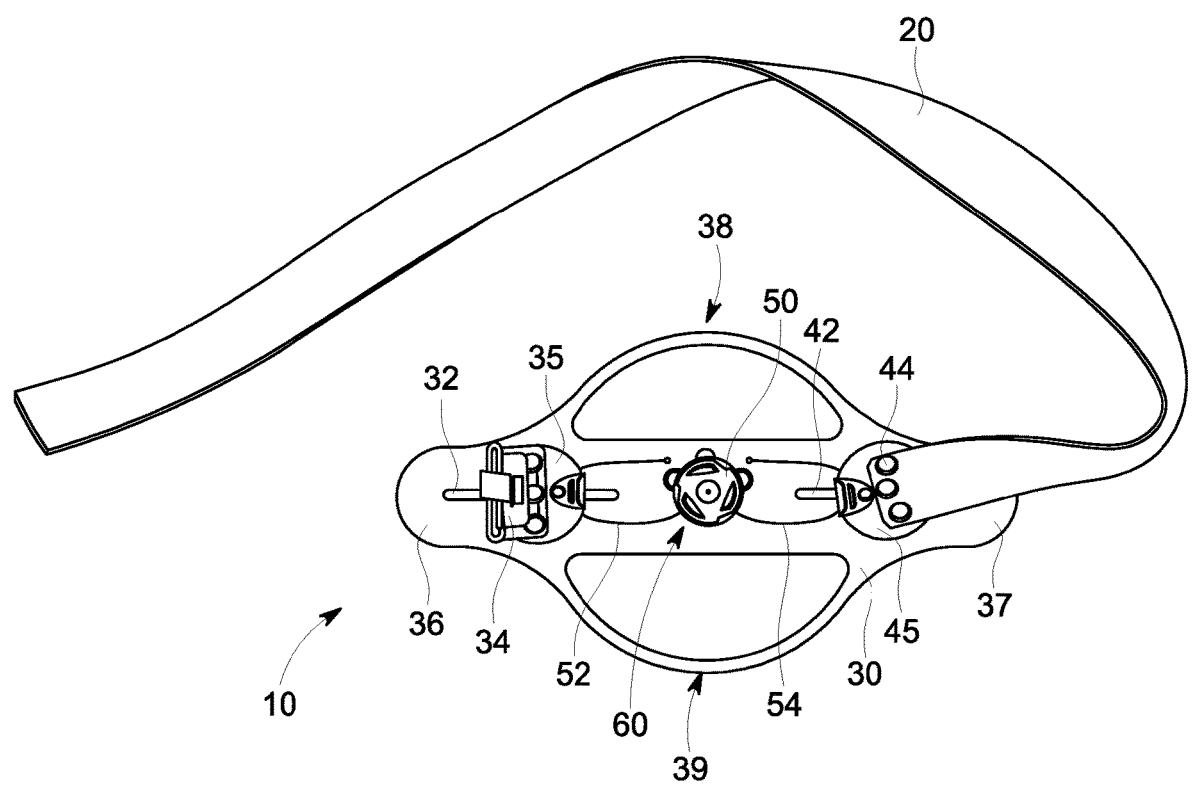
FIG. 1 is a perspective view of the belt system.

Turning to FIG. 1, a general illustration of one embodiment of the contemplated support belt 10, or lumbosacral orthosis (LSO) 10 is provided. As seen, support belt 10 includes an abdominal panel 30 which is generally circular or oval, and is specifically configured/sized to provide abdominal containment to the user. Abdominal panel 30 includes left and right horizontal slots 32, 42 which are designed to guide the end of the left and right strap toward the centrally located Boa Reel 50 that leverages and tightens waist groove belt 20. More specifically, a pair of attachment mechanisms 34, 44 include a first sliding disc 35 and a second sliding disc 45, which are coupled to abdominal panel 30 via certain posts or extensions 36, 46 (not shown) are inserted into slots 32, 42. Sliding discs 35, 45 provide multiple connection points, for various components, including the waist groove belt 20 and a tensioning mechanism 60. As illustrated, second slidable disc 45 is permanently attached to belt 20, while the first disc 35 supports a magnetic "Fidlock" unlocking buckle 34. This of connection allows for the easy donning and doffing of support belt 10. As will be appreciated, this Fidlock is one version of the connection mechanism 34 and many alternatives are possible. For example, the belt could have adjustability on one end and a closure strategy on the other end. Alternatively, both ends of the belt 2 could be adjustably attached. The particular adjustment mechanisms could also vary, depending on the features desired. A classic belt buckle structure could be used, with holes existing in the belt and a post on the sliding disks referenced above. Similarly, a ratchet mechanism, adjustable quick connect mechanisms or synch structure could be used. Those skilled in the art will recognize that many variations are possible.

As shown in the attached figure, the belt design 10 includes two forms of adjustability. Once the wearer places LSO 10 around their body and locates the waist groove belt at their waist, the first strap tensioner (i.e. connection mechanism 34) reduces the length of the strap until the slack is removed and there's total contact to the patient's body. At this point, a second tensioning mechanism 60 is activated/used. This second tensioning mechanism 60 is necessary as it was discovered that the tensioning/tightening of the inner belt strap cannot come from the left or right side as the belt is then tighter on one side than the other. When this occurs, the right is tighter than the left or vice versa. Using second-tensioning mechanism 60 contemplated, a symmetrical tightening can occur by operating the second tensioning mechanism 60 to a desired compression which will then provide comfort and pain relief.

As best illustrated in FIG. 1, second tensioning mechanism 60 in this embodiment, includes a Boa reel 50 and cooperating cables 52, 54, and is utilized to allow for the above mentioned adjustability. In the illustrated embodiment, second tensioning mechanism 16 a first cable 52 and a second cable 54, movably coupled to each of sliding discs 35, 45, and a tensioning wheel 50 which can adjust the length of the cable. In one situation, the length of the cable is shortened, which creates an inward pulling of discs 35, 45. This inward motion or inward pulling of cable 32 and 54, causes sliding discs 35, 45 to be pulled closer to one another and consequently increases the tension on the waist groove belt 20, when worn by a user. In this manner, the tension of the overall support belt can be easily adjusted by a user without requiring detachment or removal.

As suggested above, waist groove belt 20 is specifically designed to fit within a user's waist groove. It has been found that this positioning is particularly beneficial in providing general user support to the abdominal region. In addition, waist groove belt 20 is formed of a material and shaped to make it curve into the body without "cutting" in and causing pain. Depending on the physique of the patient, the waist grove belt 20 may be used with or without a pad or a padded sleeve much like a pad on a shoulder strap on a carry bag.

In addition to the details discussed above, abdominal panel 30 is specifically sized and designed so abdominal support is provided in a predetermined manner. More specifically, abdominal support or pressure is provided at both an upper edge 38 and a lower edge 39 of abdominal panel 30, in conjunction with the pressure provided by waist groove belt 20. In this manner, the overall system 10 provides multiple points of support. In one embodiment, a "three-point" support system is provided, with appropriate pressure being applied by the belt and abdominal panel. Specifically, pressure is applied to the users back, at upper edge 38 of the abdominal panel 36, and at the lower edge 39 of the abdominal panel 30. Further, the abdominal panel has tabs or ears 36, 37 that extend laterally, increasing the horizontal length. In use, these tabs allow guided travel along the length of the slots as the discs get pulled toward the tensioning/tightening mechanism 60, which centrally located on abdominal panel 30. The tabs 36, 37 then act like an extension of waist belt 20 as they have a similar width and continue to conform and curve in only one direction.

In use, the engaged a three point force system causes force to be applied at top edge 38 and bottom edge 39 abdominal panel 30, which are higher and lower, respectively, than the opposing force created by waist groove strap 20. This three point force system is applied in combination with intra-cavity compression, with belt 20 compressed above the crest of the hip (pelvis) and below the 12th rib (or rib cage). This is also in conjunction with the abdominal compression caused by abdominal panel 30. It is noted that this does not include compression to the rib margin anteriorly. From a very general perspective, the above mentioned three point force system creates abdominal compression which opposes a lumbar pull. This results in superior intra-cavity compression, which counters and effectively distracts the spinal column (or axial unloads the lumbar spine). As a result, a mass of tissue is compressed and contained within the skeleton structure of the body, which facilitates an unloading response and a sagittal (side view) extension of the spine. Further, this creates spacing (or elevation) between the vertebra, resulting in pain relief (or relief of symptoms). As can be appreciated, the specific size and dimensions of the abdominal panel create this unique treatment or therapy.

Figure 3:
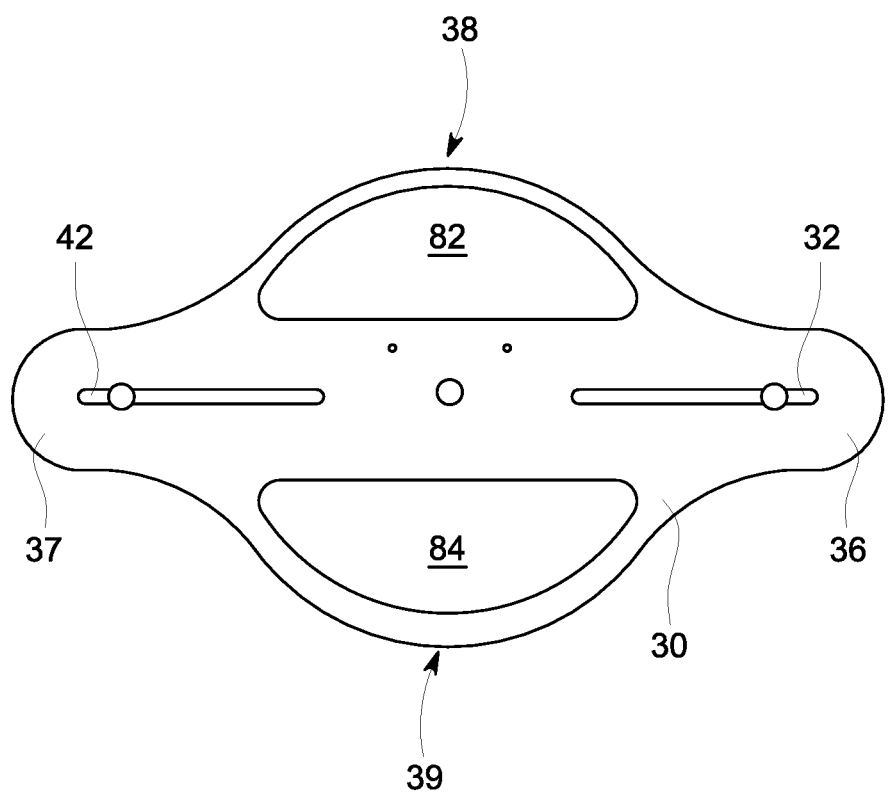
FIG. 3 is a rear view of the abdominal panel illustrated in FIG. 2.

As mentioned above, the three point force system provides certain advantages and features which are not present in typical support belt devices. The use of additional padding and contours can further adjust to provide additional support characteristics. Referring now to FIG. 3, which illustrates an inside or rearview of abdominal panel 30. As previously discussed, abdominal panel 30 includes a central region which is cylindrical and specifically configured so that forces are provided by an upper edge 38 and a lower edge 39. Extension tabs 36 and 37 help to distribute forces in a preferred manner. In addition to these features, an upper support pad 82 is included in an upper portion of abdominal panel 30. Similarly, a lower support pad 84 is positioned in a bottom inner portion of abdominal panel 30. As will be appreciated, both upper support pad 82 and lower support pad 84 will be in contact with the users body. These components can be configured so that the pressure can be distributed and applied in a predetermined/preferred manner. As will also be appreciated, various related padding in a force distribution components can easily be included.

Figure 4:
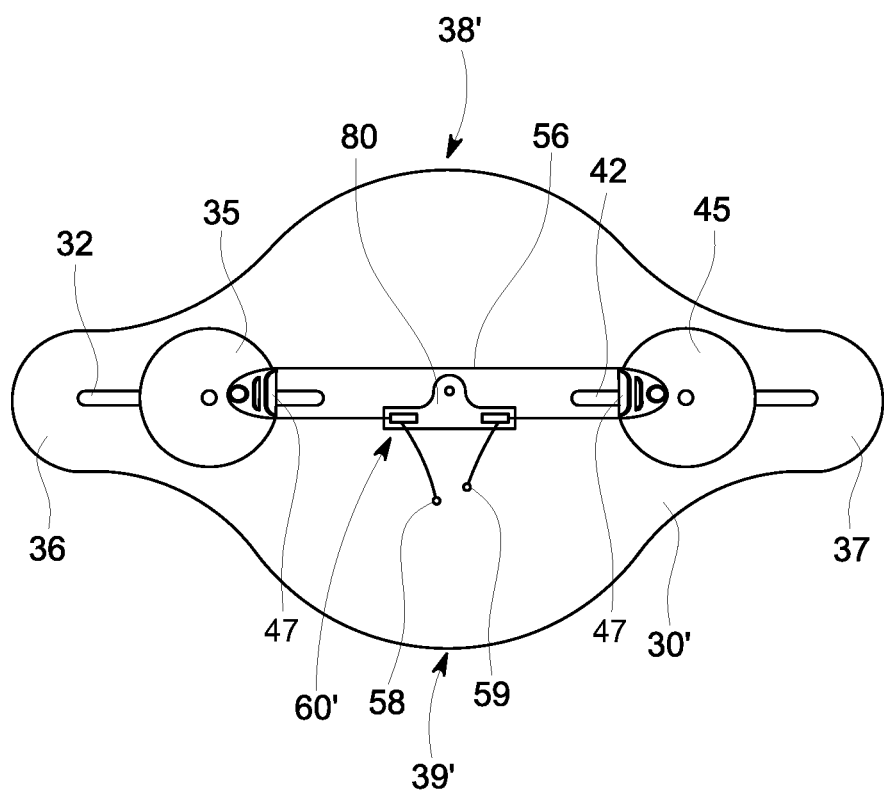
FIG. 4 is a front view of an alternative embodiment illustrating a modified abdominal panel design.

As can be easily appreciated, the configuration of abdominal panel 30 can be adjusted or modified to alter or tailor the forces applied. Referring to FIG. 4, an alternative embodiment of the abdominal support system is shown. More specifically, FIG. 4 illustrates an alternative abdominal panel 30' which has been slightly reconfigured to provide a slightly modified three point force system. FIG. 4 also does not include waste belt 20 for simplicity purposes. In this particular embodiment, abdominal panel 30' has a substantially oval shaped central portion which is specifically designed so that upper edge 38' and lower edge 39' will provide forces as described above. Tabs or ears 36, 37 are similar to those to those discussed above, and also provide the same type of forces. Also illustrated is a tensioning system 60' in this particular embodiment, a first disk 35 and a second disk 45 are again utilized to provide a sliding component. Each of these disks are slidably attached to abdominal panel 30' and make use of first groove 32 and second groove 42. Although not illustrated in FIG. 4, attachment to a waste belt 20 will also be carried on first disk 35 and second disk 45.

As mentioned above, an alternative tensioning system 60' is utilized in this embodiment. Here, cable 56 is coupled with first disk 35 and second disk 45 via a containing clip 47 positioned on each disk. Also this embodiment utilizes a clasp mechanism 80 which is attached to a central portion abdominal panel 30' so that its position will be maintained. Coupling mechanism 80 had a first clasp 82 and a second clasp 84 positioned on a face thereof which are both configured to capture and hold portions of cable 56. In one example, these clasping mechanisms could be simply spring loaded levers which allow one way movement of cable 56 while also preventing reverse movement. At opposite ends of cable 56 are knobs, which allow a user to pull on both ends. More specifically, knob 58 is connected at one end while knob 59 is connected at an opposite end. As will be appreciated, pulling on either knob causes cable 56 to provide force to both disk 35 and disk 45, thus providing the desired tensioning methodology, so that forces are evenly applied to both sides.

Figure 2:
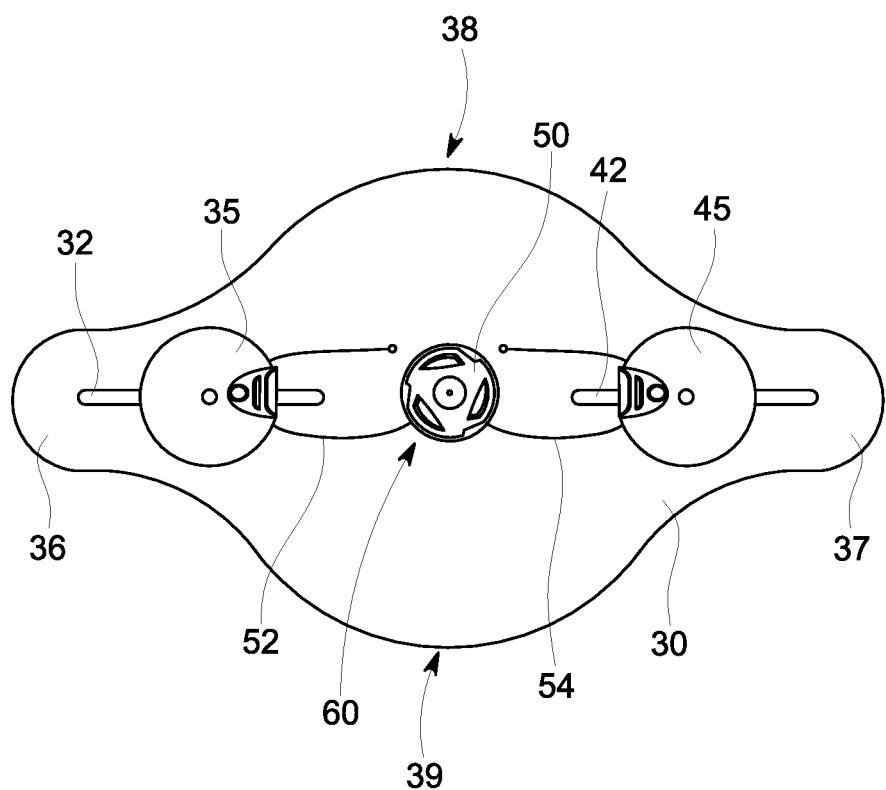
FIG. 2 is a front view of a first embodiment of the abdominal panel itself, with the belt removed.

In addition to the alternative tensioning mechanism, it will be also be apparent that abdominal panel 30' is smaller than abdominal panel 30 illustrated in FIGS. 1-3. This illustrates that the configuration of abdominal panel 30' is specifically configured to provide desired force profile, while also allowing for different fittings or different applications depending upon the size of the patient. That said, the same three point force system can be utilized to provide therapy, pain relief and rehabilitation.

Again, the lumbosacral orthosis described utilizes a three point force system wherein the anterior (front) abdominal panel has a higher and lower margin as compared to the apposing strap force that is centrally located posteriorly within the lumbar region of the patient's body.

It should be noted that this off-the-shelf lumbar sacral orthoses which utilizes the combination of an abdominal panel and circumferential waist groove strap as described herein. Those skilled in the art will recognize that it is much more common to have higher posterior panel and a narrower abdominal panel or belt, thus promoting and encouraging a flexion posture rather than a desire neutral sagittal plane alignment. When the illustrated orthosis is tightened as described above however, it proves a restriction to forward flexion and also includes an axial unloading effect on the spine. The combination of intracavity compression along with the design elements and features provides a desired motion control and pain relief mechanism for the user.

Therapeutic Application:

As suggested above, the adjustable buckling mechanism illustrated in FIG. 1 (e.g. the magnetic buckle release 34 shown in the FIG. 1) is used to first attain the proper belt length so the belt 20 can be appropriately sized and positioned around the user's waist. It is beneficial to use the adjustable buckling mechanism so that the belt is snug and held in place before any compression forces are applied. Once appropriately positioned, the tensioning mechanism 60 (i.e. boa tightening mechanism) can be used to evenly create compression and support as discussed above. By using the boa mechanism 60, the belt is evenly tightened from both sides, thus creating a uniform application of pressure to the user's abdomen.

The LSO 10 with waist groove strap discussed above can also be used with a traditional LSO outer belt. In this combination, the inner belt (i.e. the LSO 10 discussed above) provides maximal sagittal plane motion to appose flexion of the lumbar spine, while the outer belt provides a circumferential compression abdominal compression. Additionally, the outer belt can be provided with a posterior lumbar support and lateral supports for more motion control. The outer belt would be applied after the donning the inner belt. The outer belt would wrap around the anterior closure as typically applied and then would be tensioned a posterior lacer with a thumb pull. The anterior/front of the outer belt has an oval horizontal slot that accommodate a need pass through for the Boa reel.

This unique application allows the wearer to use the inner belt and abdominal panel independently of the outer belt while standing, walking, going through physical therapy and strengthening, as these physical activities do not require the gross spinal flexion in contrast to sitting postures. However, when and if the user will be sitting, he/she would benefit from the use of the combination of the inner and outer belts for greater circumferential compression, immobilization and spinal extension.

Various embodiments of the invention have been described above for purposes of illustrating the details thereof and to enable one of ordinary skill in the art to make and use the invention. The details and features of the disclosed embodiment[s] are not intended to be limiting, as many variations and modifications will be readily apparent to those of skill in the art. Accordingly, the scope of the present disclosure is intended to be interpreted broadly and to include all variations and modifications coming within the scope and spirit of the appended claims and their legal equivalents.

The invention claimed is:

1. An abdominal sacral belt providing focused support to a user, comprising:
   an abdominal panel having a substantially oval configuration with an inner surface, an outer surface and at least one slot therein, the abdominal panel formed from a partially rigid material such that limited amounts of deflection will result when exposed to uneven forces;
   an attachment disc slidably attached to the outer surface of the abdominal panel;
   a waist belt having a first end attached to the attachment disc and a second end removably attachable to the outer surface of the abdominal panel, the waist belt having a width configured to fit within a waist groove of the user, and having a length adapted to fit around the waist of the user when the second end is attached to the outer surface of the abdominal panel; and
   an adjustment mechanism coupled to the outer surface of the abdominal panel and further coupled to the attachment disc, the adjustment mechanism having an actuator configured to be operable by the user to cause the attachment disc to continuously slide relative to the abdominal panel, and thus to cause the waist belt to be smoothly tightened around the waist of the user;
   wherein the abdominal panel is configured such that, when the waist belt surrounds the waist of the user and is positioned within the waist groove and the inner surface of the abdominal panel is adjacent the user's abdomen, an upper edge of the abdominal panel is positioned at an upper support location which is spaced above the waist groove of the user and a lower edge of the abdominal panel is positioned at a lower support location which is spaced below the waist groove of the user, and wherein the waist belt and the abdominal panel create a three point support system when applied to the user, wherein operation of the adjustment mechanism and the resulting smooth tightening of the waist belt will thereby provide desired levels of pressure to be applied to the upper support location, the lower support location and the user's back along the waist groove of the user.

2. The abdominal sacral belt of claim 1 wherein the adjustment mechanism is a boa mechanism operable from the outer surface of the abdominal panel and coupled to the attachment disc via a cable.

3. The abdominal sacral belt of claim 1 wherein the abdominal panel has a linear region between the upper edge and the lower edge.

4. The abdominal sacral belt of claim 3 wherein the abdominal panel is arcuate from side to side, thus conformable to the user's body in response to tightening of the waist belt around the user's waist.

5. The abdominal sacral belt of claim 4 wherein the adjustment mechanism is a boa mechanism operable from the outer surface of the abdominal panel and coupled to the attachment disc via a cable in a manner to cause the tightening of the waist belt around the user's waist when the boa mechanism is operated.

6. The abdominal sacral belt of claim 3 wherein the linear region between the upper edge and the lower edge has a predetermined level of flexibility thereby insuring that predetermined levels of pressure can be applied at the upper and lower edges.

7. The abdominal sacral belt of claim 6 wherein the abdominal panel has a predetermined level of flexibility from side-to-side, wherein the side-to-side level of flexibility is greater than the predetermined level of flexibility between the upper edge and the lower edge, thereby allowing the abdominal panel to be conformable to the user's body in response to tightening of the waist belt around the user's waist.

8. An abdominal sacral orthosis providing three point support to a user, comprising:
   a partially rigid abdominal panel having an upper edge and a lower edge, wherein the panel is formed to have a predetermined level of flexibility;
   a waist belt having a width configured to fit within a waist groove of the user and having a length adapted sized to fit around the waist of the user;
   a pair of attachment mechanisms adjustably coupled to the abdominal panel and attachable to a first end of the waist belt and a second end of the waist belt, respectively, thus allowing the user to place the orthosis around their waist with the abdominal panel placed upon the user's abdomen and the waist belt snuggly wrapped around the user's waist and positioned within the waist groove; and
   a tightening mechanism coupled to on an anterior surface of the abdominal panel and cooperating with the pair of attachment mechanisms, the tightening mechanism adapted to cause the waist belt to be evenly tightened from both the first end and the second end of the waist belt when operated, thus resulting in the three point support to be provided to the user when positioned such that the waist belt is within the waist groove of the user and the abdominal panel is placed upon the user's abdomen, with the three point support achieved by compressive forces which are exerted at both the upper edge and the lower edge of the abdominal panel, and around the waist of the user, wherein the upper edge is positioned a predetermined distance above the user's waist groove and the lower edge is positioned a predetermined distanced below the waist groove.

9. The orthosis of claim 8 wherein the tightening mechanism is a boa mechanism operable from the anterior surface of the abdominal panel and coupled to the pair of attachment mechanisms via a cable.

10. The orthosis of claim 9 wherein the pair of attachment mechanisms allow for the releasable attachment of at least the first end of the waist belt or the second end of the waist belt.

11. The abdominal sacral orthosis of claim 8 wherein a region of the abdominal panel between the upper edge and the lower edge is liner such that the linear region insures that predetermined levels of pressure can be applied at the upper and lower edges, and wherein the predetermined level of flexibility of the abdominal panel in a side-to-side directions allows the abdominal panel to conform around the user's waist when tightened.

12. The orthosis of claim 11 wherein the tightening mechanism is a boa mechanism operable from outer surface of the abdominal panel and coupled to the pair of attachment mechanisms via a cable.

* * * * *

UNITED STATES PATENT AND TRADEMARK OFFICE
CERTIFICATE OF CORRECTION

PATENT NO. : 11,452,632 B2
APPLICATION NO. : 16/612741
DATED : September 27, 2022
INVENTOR(S) : Kramer et al.

Page 1 of 1

It is certified that error appears in the above-identified patent and that said Letters Patent is hereby corrected as shown below:

In the Claims

Column 7 Line 11 In Claim 8, after "adapted", delete "sized".

Column 7 Line 21 In Claim 8, after "a tightening mechanism coupled", delete "to".

Signed and Sealed this
Tenth Day of January, 2023

Katherine Kelly Vidal
*Director of the United States Patent and Trademark Office*